United States Patent
Meijer

(10) Patent No.: US 7,634,301 B2
(45) Date of Patent: Dec. 15, 2009

(54) REPEATED EXAMINATION REPORTING

(75) Inventor: Eric L. Meijer, Best (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 349 days.

(21) Appl. No.: 10/571,747

(22) PCT Filed: Sep. 1, 2004

(86) PCT No.: PCT/IB2004/051665

§ 371 (c)(1),
(2), (4) Date: Mar. 14, 2006

(87) PCT Pub. No.: WO2005/026973

PCT Pub. Date: Mar. 24, 2005

(65) Prior Publication Data

US 2007/0064981 A1    Mar. 22, 2007

Related U.S. Application Data

(60) Provisional application No. 60/503,709, filed on Sep. 17, 2003.

(51) Int. Cl.
*A61B 5/00* (2006.01)
*G06K 9/00* (2006.01)
(52) U.S. Cl. .................. 600/407; 382/128; 600/410
(58) Field of Classification Search ............... 600/407, 600/437, 300, 425–427, 523, 509, 408; 705/2, 705/3; 378/65; 382/128, 191, 132; 707/10, 707/102; 713/189, 193
See application file for complete search history.

(56) References Cited

U.S. PATENT DOCUMENTS

| | | | |
|---|---|---|---|
| 5,581,460 A | 12/1996 | Kotake et al. ............. 295/203 |
| 5,740,267 A | 4/1998 | Echerer et al. ........... 382/132 |
| 5,779,634 A * | 7/1998 | Ema et al. ................ 600/407 |
| 5,878,746 A | 3/1999 | Lemelson et al. ....... 128/653.1 |
| 6,317,617 B1 | 11/2001 | Gilhuijs et al. .......... 600/408 |
| 6,379,306 B1 * | 4/2002 | Washburn et al. ....... 600/454 |
| 7,065,235 B2 * | 6/2006 | Dewaele .................. 382/132 |
| 2002/0198447 A1 | 12/2002 | Van Muiswinkel et al. .. 600/410 |
| 2003/0206646 A1 * | 11/2003 | Brackett .................. 382/128 |
| 2003/0236458 A1 * | 12/2003 | Hochman ................ 600/431 |
| 2004/0005027 A1 * | 1/2004 | Nafstadius ............... 378/65 |
| 2004/0122702 A1 * | 6/2004 | Sabol et al. ............. 705/2 |
| 2005/0147284 A1 | 7/2005 | Vining et al. ............ 382/128 |

FOREIGN PATENT DOCUMENTS

| | | |
|---|---|---|
| CN | 1313569 | 9/2001 |
| WO | WO 02/39891 A1 | 5/2002 |

* cited by examiner

*Primary Examiner*—Eric F Winakur
*Assistant Examiner*—Lawrence N Laryea

(57) ABSTRACT

A plurality of diagnostic images of a region of interest of a subject are generated and stored in a patient database (10). In one of the images, a region of interest, such as a tumor, is identified. The database is searched for the other images of the same region of interest. Parameter values indicative of characteristics of the tumor are extracted from each image and displayed in tabular or graphic format by time. The images are reformatted, scaled, and displayed in a cinè format to illustrate a temporal evolution of the tumor in the region of interest.

15 Claims, 3 Drawing Sheets

REPEATED EXAMINATION REPORTING

CROSS REFERENCE TO RELATED APPLICATIONS

This application claims the benefit of U.S. provisional application Ser. No. 60/503,709 filed Sep. 17, 2003, which is incorporated herein by reference.

DESCRIPTION

The present invention relates to disease or physical condition analysis and reporting. It finds particular application in conjunction with monitoring disease or physical progression over time and will be described with particular reference thereto. It is to be appreciated, however, that the present invention is applicable to cross patient studies, and other applications as well.

There is a long standing interest in tracking the progression of disease and physical conditions of patients. When a patient is initially diagnosed, the speed with which a condition is progressing affects a prescribed treatment regimen. After a patient receives a regimen of treatment, follow-up visits ascertain the quality and effectiveness of the prescribed treatment, whether other courses of action are in order, and the like. A significant portion of this patient tracking and continued diagnosis occurs in the realm of diagnostic imaging. A patient with symptoms is diagnosed or a diagnosis is confirmed using an imaging procedure.

Today, a patient's medical records are typically maintained in a computer database. The record includes previous diagnostic images, although the prior images are often of differing regions of the body and were generated with imaging parameters and in imaging modalities geared for other types of examinations. Nonetheless, the diagnosing physician can page through the images in the patient's file manually to look for images that include the same region and might provide insights into the development of the problem. Further, after or during the treatment, the patient may return for further imaging to assess the success of the treatment. The physician can retrieve prior images at various stages in the treatment and display them, side by side with the current image. The physician can visually compare the latest image with the previous image or previous images with each other. The progression of the images aids the physician in making a determination about the rate of progress of the malady and success of the treatment.

Currently, the images to be compared are displayed concurrently in separate windows on a computer monitor, or similar display device. This can be cumbersome, and the progression of the region of interest can be intuitively difficult to follow. Additionally, the images often were taken at different time intervals and have a different scale, perspective, contrast, and other image properties. For instance, two images of an irregularly shaped brain tumor taken from different angles may show the tumor as being different sizes. In such a scenario, it would be difficult to tell whether the tumor actually changed in size, or if one viewed image was taken through a slice in which a direction in which the tumor is wider.

Although imaging sequences and scans can be saved and reproduced, it is difficult to accurately reproduce the physical position of a patient within a scanner on different days. Slightly different patient positions from scan to scan will result in slightly different image perspectives, given the exact same imaging scan or sequence.

More factors are introduced if a physician attempts to do a cross-modality comparison. For instance, the patient with the brain tumor may have a current MRI and an older CT scan that includes the region. Different modalities emphasize different tissue properties and may show the tumor with different degrees of differentiation relative to the surrounding tissue.

The present application contemplates a new and improved object identification system, which overcomes the above-referenced problems and others.

In accordance with one aspect of the present invention, a diagnostic image processing system is provided. A parameter extraction processor extracts selected parameter values from a diagnostic image representation or from data for generating the diagnostic image. A subject database stores the image representation and the extracted parameter values in association with at least a patient identity and a date. The database is updated each time the subject is imaged. A report formatting means formats the extracted parameter values from a plurality of diagnostic images generated at different times into a report.

In accordance with another aspect of the present invention, a method of diagnostic image processing is provided. A diagnostic image representation is displayed and a region of interest is selected on the display. Parameter values from the selected region are extracted. The image representation along with the extracted parameter values are stored in a database in association with at least a subject identity and a date. The extracted parameter values from a plurality of diagnostic images are formatted into a report.

One advantage of the present invention resides in improved patient progress tracking.

Another advantage resides in improved patient diagnosis and treatment planning.

Another advantage resides in a more intuitively meaningful image display.

Another advantage results in easier cross-modality scan comparison.

Another advantage resides in easier scan result comparison.

Still further advantages and benefits of the present invention will become apparent to those of ordinary skill in the art upon reading and understanding the following detailed description of the preferred embodiments.

The invention may take form in various components and arrangements of components, and in various steps and arrangements of steps. The drawings are only for purposes of illustrating the preferred embodiments and are not to be construed as limiting the invention.

Figure 1:
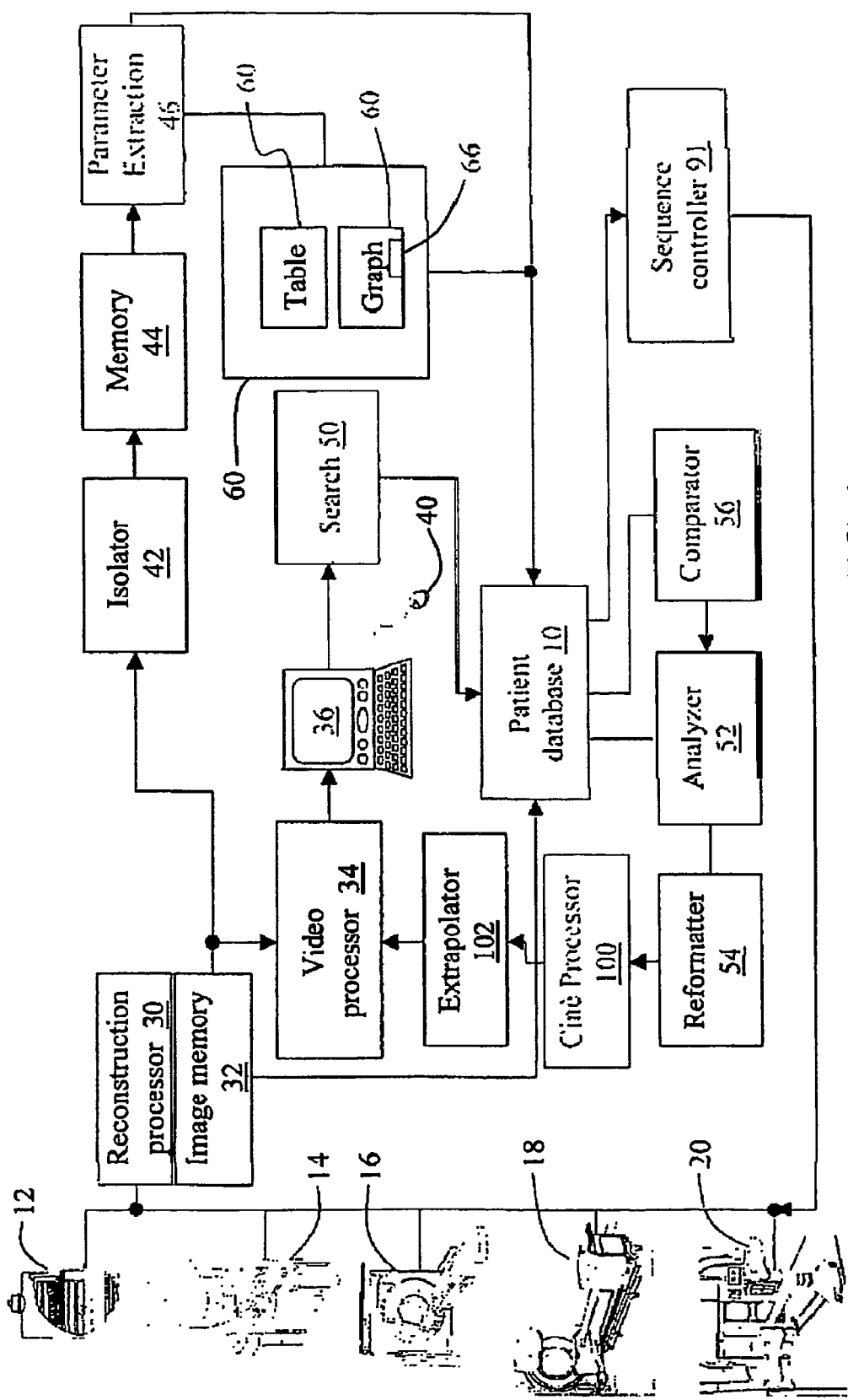
FIG. 1 is a diagrammatic illustration of an imaging system with repeated examination capabilities.

With reference to FIG. 1, a variety of diagnostic imagers are connected with a hospital database 10. Preferably, the diagnostic imagers include a high field magnetic resonance (MR) scanner 12, a low field MR scanner 14, a CT scanner 16, a nuclear camera 18, and a digital x-ray system 20. Other diagnostic imaging equipment is also contemplated. Each diagnostic imager includes or is associated with a reconstruction processor for implementing reconstruction algorithms for the corresponding modality. Typically, selected reconstructed images are saved into the patient's record in the hospital database 10 rather than the underlying data although either or both can be. The images, preferably volume images, are stored with an electronic indication of the imaged region.

Looking to the high field magnetic resonance scanner 12 by way of example, the data from the scanner is reconstructed by a reconstruction processor 30 and stored into an image memory 32. A video processor 34 withdraws selected portions of the reconstructed image for display on a video or other human readable monitor 36. The other scanners include similar reconstruction processors, image memories, video processors, and displays.

Using a mouse 40 or other suitable pointing and drawing means, the operator outlines the region of interest on a displayed image or otherwise indicates the region of interest. Taking the monitoring of a tumor, by way of example, a processor or means 42 isolates the designated tumor from the surrounding tissue. This may be done by comparing gray scale or other properties of the designated tumor relative to the surrounding tissue in the diagnostic image memory. The generated isolated image of the tumor of interest is stored in a memory 44 which is examined by a parameter extraction processor or means 46 that extracts parameters of the isolated tumor such as its volume, average density, blood flow rate to or through it, diffusion coefficients, fractional diffusion anisotropy values, spectroscopic values, metabolic information, and the like. The extracted parameters are preferably stored with the image data in the patient database 10 to facilitate the comparison of these parameters with similar parameters derived from earlier or later images.

To monitor the progress of the tumor, the operator initiates a program 50 which searches the hospital database 10 for other images of the same patient which include the region surrounding the tumor. Images of the region of the patient which include the tumor are analyzed 52 to isolate the tissue which is at the same location as the tumor.

Once the corresponding portion of the archived images has been located, a reformatting means 54 reformats the images to convert the images to the same viewing direction such as with a multi-planar reformatting technique which re-grids the images and scales the reformatted images as the present examination images. The reformatted images of the same region of interest are then provided to the video processor 34 for display on the monitor 36. The isolating means 42 is then used manually or automatically to isolate the tissue at the same location as the tumor with similar grayscale, MR number, or other similar characteristic. Preferably, the isolating means goes to the same location and tries to isolate a tumor with the same physical properties. The automatic isolating means may or may not be successful. For example, some of the images may have been taken before there was a tumor. Others may have been taken in a modality in which the tumor is hard to distinguish. Also, the tumor may have grown eccentrically. That is, in early images, the tumor could have been displaced from the current center of mass and the program may be missing it. The diagnosing physician uses the cursor 40 to outline regions of potential interest on each of the archived images for isolation and analysis.

Some of the retrieved archived images may have been stored with a coordinate shift relative to the current diagnostic image. In one embodiment, the operator manually designates a corresponding point in each image and a reformatting means 54 shifts the images to align the common points. In another embodiment, a pattern comparing means 56 compares the images of generally similar regions of the subject by isolating common landmark points, the pattern means 56 determines a transform which translates the images into registration.

Once the prior images have been retrieved and the corresponding regions registered and the tumor or other tissue of interest isolated, the parameters extracted by the parameter extraction means 46 are sent to a report formatting processor or means 60. The report formatting means 60 includes a plurality of report generation options. The extracted values are ordered by the data compilation processor 60 and placed into a repeated examination report, that is, they are placed in an intuitive visual format, preferably according to date. Charts, tables, graphs and other comparable display formats are suitable for presenting the extracted values. For example, in a patient who has a brain tumor, one of the likely extracted values would be size of the tumor. A chart that shows the size of the brain tumor as a function of time would be one exemplary mode of display. Not all values will be available in every imaging modality. Preferably, dates corresponding to data points with no data are omitted from the presentation of that value. More specifically, a table option 62 generates a table which sets forth corresponding parameters of interest from each of the preceding images. For example, the table could set forth the volume of the tumor in each image, the date of the image, etc. in tabular format. A graphing means or algorithm 64 presents a selected parameter of the tumor, such as volume or tissue density, and plots the change in that parameter versus time. Because the prior images have probably not been taken at regular periodic images, the graphing processor includes a means 66 for scaling the time between exams to make the timeline of the graphs linear, logarithmic, or the like.

Of course, for retrieved images that were stored after treatment commenced, the parameter extraction means may simply extract the measured parameters which were stored with the images.

Figure 2:
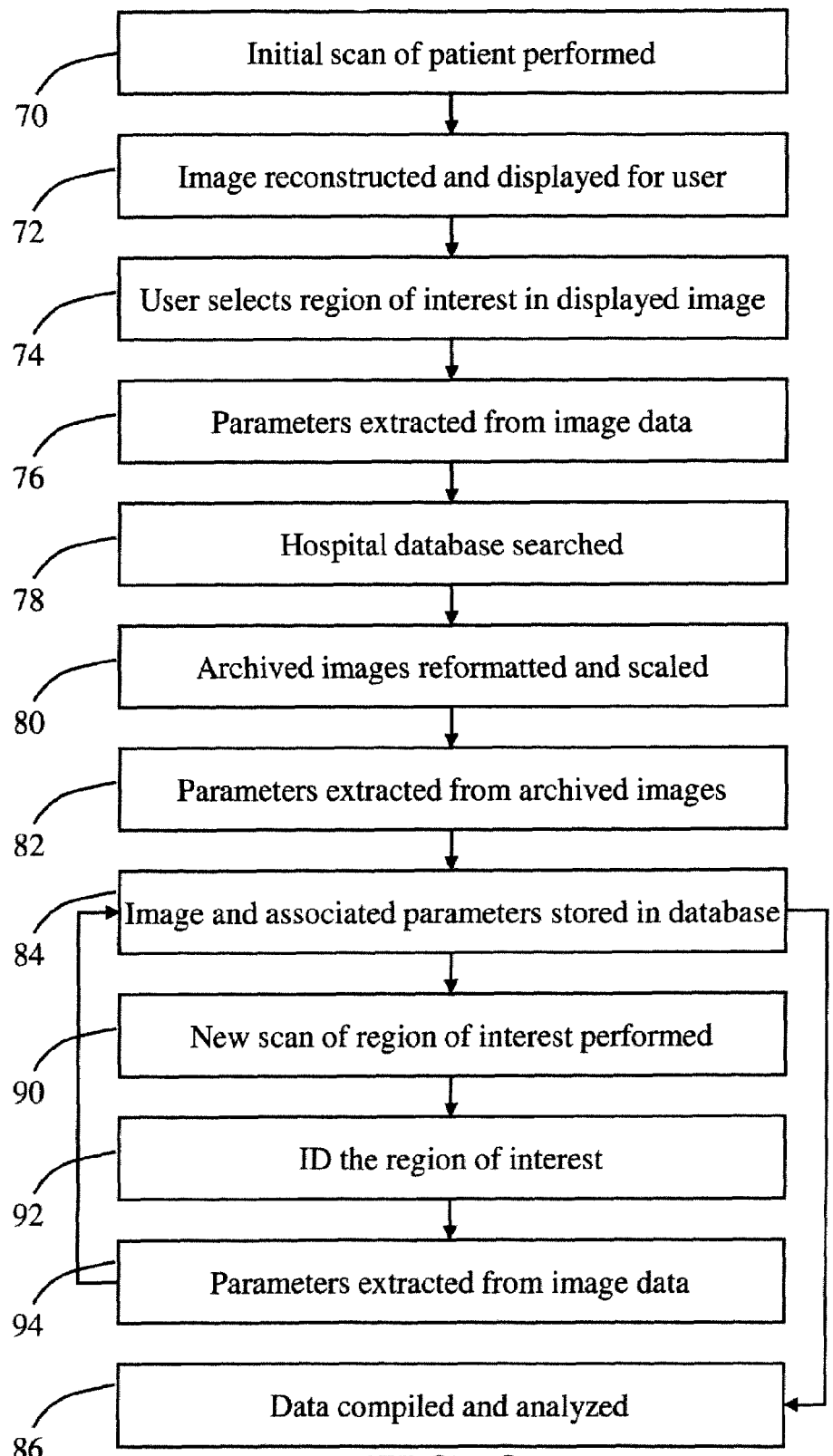
FIG. 2 is a flow diagram illustrating the construction of a repeated examination report; and, FIG. 3 is an exemplary report format including a graphical representation of a progression vs. time.
Figure 3:
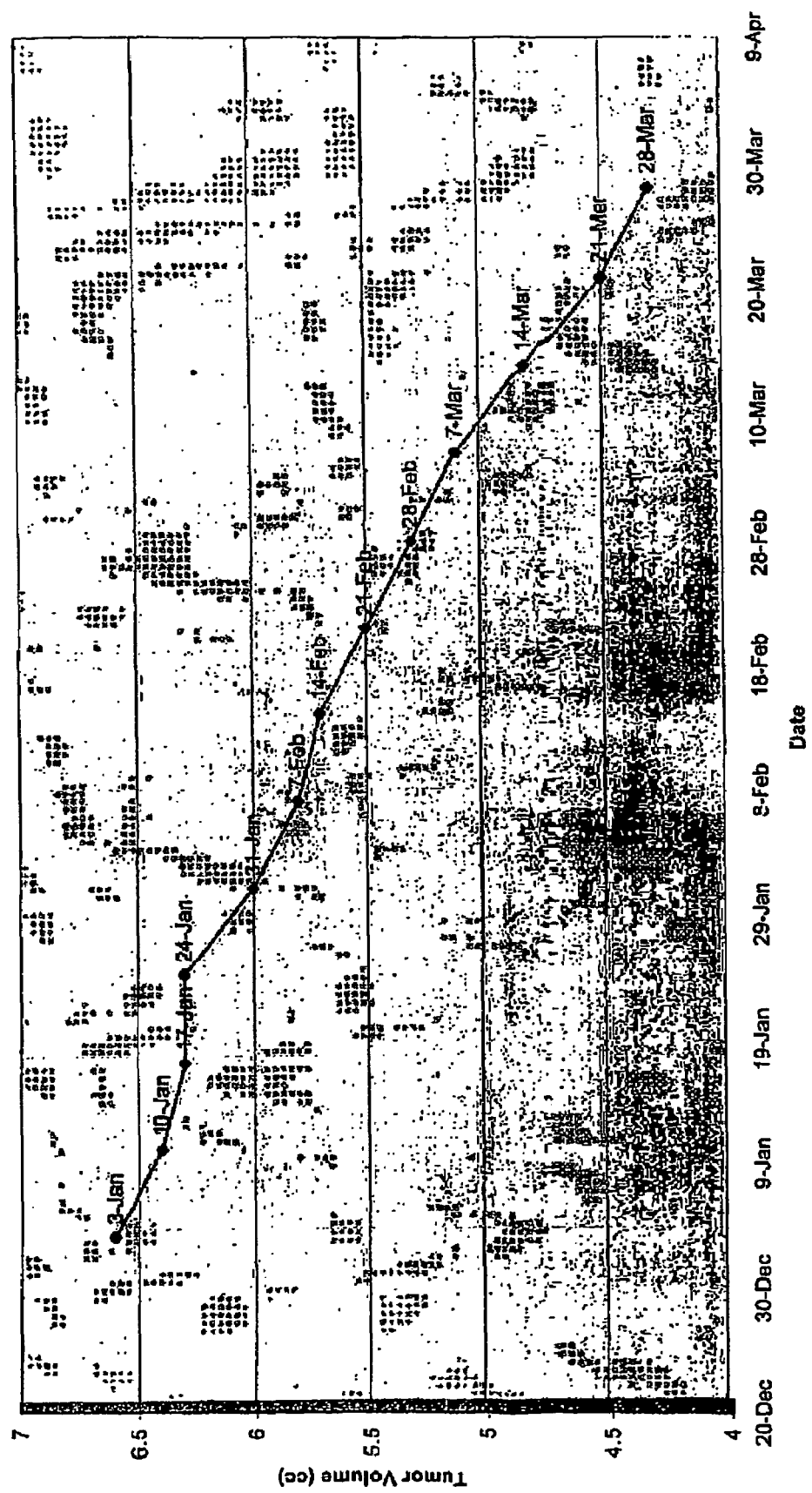

Over time, patients may be imaged repeatedly, with multiple image modalities. With reference to FIG. 2, the process for incorporating further scans of the patient into the patient database 10 is illustrated. Before beginning a patient's treatment, an initial scan of the patient is performed 70. An image is reconstructed and displayed for the user 72. The user then selects a region of interest of the image 74. Preferably, the region includes a portion of a static body structure, to aid in future image registrations. After the region of interest is selected, selected image parameters are then withdrawn from the image 76. The hospital database 10 is searched 78 for prior images of the same region of the subject. These archived images are reformatted and scaled 80. The same regions of each image are analyzed, either automatically or manually, and the selected parameters are extracted 82. The extracted parameters are stored 84 in the patient database 10. Once the parameters have been extracted and stored, they need not be extracted again. Of course, if new extraction techniques are developed, the extraction process can be repeated. The extracted parameters are formatted 86 into a report format such as a table or a graph as illustrated in FIG. 3. The reports are used by the physician to confirm a diagnosis, plan treatment, and the like.

After the scan, the patient receives the prescribed therapy, e.g. chemotherapy or oncological radiation therapy. Alternately, the "treatment" may simply be the passage of time, such as allowing a broken bone to mend. In either case, periods of time lapses between diagnostic image sessions, to allow the region to respond to the administered treatment, whether it is active or passive. After sufficient time has elapsed, a new scan of the region of interest is performed 90. If the same scan is desired, a sequence controller 91 accesses the patient database 10 to retrieve the sequence used to generate the baseline image and recreates that sequence. Alternately, a different sequence may be used, generating different geometries or resolutions, or a different modality entirely may be used. In either instance, downstream software identifies 92 the corresponding region of interest in a subsequent image. Parameters are extracted 94 from the new raw data set and image and are, in turn, stored 84 in the patient database 10 according to patient ID and date. If different parameters are extracted, the prior images are retrieved from the patient database 10 and the new parameters are extracted from them. After each imaging session the report and the database 10 are updated to chart the progression of the region of interest over time.

In another display embodiment, with reference again to FIG. 1, when a set of images and corresponding data values are selected for viewing, the registration processor 54 reformats and registers the retrieved images to the baseline image. Preferably, the image is translated, rotated, and uniformly scaled to bring it into alignment with the original image. Once all images are registered, they are displayed to the user in an intuitive format. For example, all the images in order by time are displayed on the user interface 36 concurrently. In another example, a cinè processor 100 processes the images for display in a cinè mode, showing an action progression of the region of interest over time. To supplement the cinè mode, an extrapolator 102 compares the images, and their dates, and extrapolate intermediate sub-images between the actual images as needed to generate all the image frames for a cine display with a linear or other selected timeline. The extrapolator 102 creates images based on a real time scale (e.g. one frame per week) to aid in visual intuitiveness.

The invention has been described with reference to the preferred embodiments. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A diagnostic image processing system comprising:
  a user interface with which a user selects a region of interest of at least one baseline diagnostic image of a current patient having a current patient identity from which parameter values are to be extracted;
  a subject database that stores diagnostic images generated at different times each in association with at least a patient identity and a date, the subject database being updated each time a patient is imaged;
  a database searching means that searches the subject database with the current patient identity for the stored diagnostic images containing the selected region of interest of the current patient;
  a parameter extraction processor that extracts the parameter values from the selected region of interest of the at least one baseline image of the current patient and extracts like parameter values from the selected region of interest of the stored diagnostic images of the current patient or from data for generating the stored diagnostic images of the current patient; and,
  a report formatting means for formatting the extracted parameter values from the at least one baseline image and the stored diagnostic images of the current patient generated at different times into a report descriptive of the parameter value's development with time.

2. The system as set forth in claim 1, further including:
  an image registration processor that aligns and scales the selected region of interest of the stored diagnostic images and the at least one baseline diagnostic image of the current patient.

3. The system as set forth in claim 2, further including:
  a cinè image sequence generator that converts the selected region of interest of the baseline and stored diagnostic images into a temporally scaled sequence of cinè images.

4. The system as set forth in claim 1, wherein the report formatting means includes a graphing means for plotting change of a selected parameter versus time.

5. A method of diagnostic image processing including:
  generating diagnostic image representations of a current subject at different dates with a diagnostic imaging apparatus;
  storing the generated diagnostic image representations in a subject database catalogued by at least subject identity and date;
  generating and displaying on a monitor a baseline diagnostic image representation of the current patient;
  selecting a region of interest of the subject on the displayed baseline diagnostic image representation;
  searching the subject database with the current subject identity and retrieving the diagnostic image representations of the current subject which include the selected region of interest;
  extracting user selected parameter values from the selected region of interest of the displayed baseline and retrieved diagnostic image representations of the current subject;
  formatting the extracted parameter values from the retrieved and baseline diagnostic image representations into a report; and,
  at least one of displaying the report on the monitor and storing the report in the subject database.

6. The method as set forth in claim 5, further including:
  registering the selected region of interest of the diagnostic image representations retrieved from the subject database with the selected region of interest of the baseline image representations.

7. The method as set forth in claim 6, further including:
  displaying the registered diagnostic image representations sequentially by date.

8. The method as set forth in claim 7, further including:
  temporally interpolating the registered diagnostic image representations such that the sequentially displayed image representations are displayed with a linear time scale.

9. The method as set forth in claim 5, wherein the formatting step includes:
  presenting the selected parameter values extracted from the baseline and retrieved diagnostic image representations in tabular format by date.

10. The method as set forth in claim 5, wherein the formatting step includes:
  presenting the selected parameter values extracted from the baseline and retrieved diagnostic image representations in a graph versus time with a pre-selected time scale.

11. The method as set forth in claim 5, wherein the parameter values include at least one of:
  a volume of the selected region;
  a blood flow through the selected region;
  an average density in the selected region;
  diffusion coefficients of the selected region;
  fractional diffusion anisotropy values in the selected region; and,
  spectroscopic peak intensities in the selected region.

12. A method of diagnostic imaging comprising:
  creating an image representation of a portion of a subject with a diagnostic imaging apparatus;

with a user interface, selecting a region of the image representation for further study;

with one or more processors:

storing the image representation in a subject database cataloged by at least a subject identity and a date the image representation was generated, extracting selected parameter values from the image representation and storing them in the subject database, creating at least one other image representation of the portion of the subject on a subsequent date, extracting the selected parameter values from the at least one other image representation, storing the at least one other image representation and the parameter values extracted from the at least one other image representation in the subject database, and spatially registering the image representation and the at least one other image representation; and on a monitor, displaying the image representations to show a time progression of the region.

13. The method as set forth in claim 12, further including:

presenting the selected parameter values in one of graphical and tabular form showing a progression of the parameter values over time.

14. The method as set forth in claim 12, wherein the image representation and the at least one other image representation are produced by different modalities of diagnostic imaging and registered by aligning structures identifiable in all modalities involved, and further including:

enhancing the resolution of the image representations by utilizing complementary characteristics of the modalities involved.

15. The method as set forth in claim 12, wherein the selected parameter values include a size of a tumor and the displaying step includes showing a time evolution of the size of the tumor.

\* \* \* \* \*